United States Patent [19]

Schwartz, Jr.

[11] Patent Number: 5,580,905
[45] Date of Patent: Dec. 3, 1996

[54] PROCESS FOR RECYCLING POLYESTERS

[75] Inventor: John A. Schwartz, Jr., Spartanburg, S.C.

[73] Assignee: United Resource Recovery Corporation, Spartanburg, S.C.

[21] Appl. No.: 400,789

[22] Filed: Mar. 7, 1995

Related U.S. Application Data

[63] Continuation-in-part of Ser. No. 234,237, Apr. 28, 1994, Pat. No. 5,395,858.

[51] Int. Cl.$^6$ .................................................. C08J 11/04
[52] U.S. Cl. ............................ 521/48; 521/45; 75/417; 75/422; 75/713; 528/481; 528/489; 528/499
[58] Field of Search ......................... 521/45, 48; 75/417, 75/422, 713; 528/481, 489, 499

[56] References Cited

U.S. PATENT DOCUMENTS

| | | |
|---|---|---|
| 2,927,130 | 3/1960 | Schütt . |
| 3,047,435 | 7/1962 | Wemple ................................. 134/2 |
| 3,120,561 | 2/1964 | Chambret ........................... 562/483 |
| 3,215,735 | 11/1965 | Sakurai et al. . |
| 3,257,335 | 6/1966 | Whitfield et al. .................... 521/48.5 |
| 3,503,904 | 3/1970 | Dietz et al. .......................... 521/46 |
| 3,544,622 | 12/1970 | England ............................. 562/483 |
| 3,579,572 | 5/1971 | Amedjian et al. . |
| 3,594,414 | 7/1971 | Katzschmann ..................... 562/483 |
| 3,647,422 | 3/1972 | Wainer ................................ 204/72 |
| 3,652,466 | 3/1972 | Hittel et al. .......................... 521/46 |
| 3,873,314 | 3/1975 | Woo et al. ............................ 75/713 |
| 3,873,609 | 3/1975 | Wu et al. . |
| 3,884,850 | 5/1975 | Ostrowski ......................... 521/48.5 |
| 3,928,253 | 12/1975 | Thornton et al. ................... 521/46 |
| 3,952,053 | 4/1976 | Brown, Jr. et al. . |
| 3,953,502 | 4/1976 | Fassell et al. ..................... 562/483 |
| 3,956,088 | 5/1976 | Fassell et al. ..................... 204/109 |
| 4,078,143 | 3/1978 | Malik et al. ....................... 560/78 |
| 4,163,860 | 7/1979 | Delattre et al. ................... 560/96 |
| 4,201,871 | 5/1980 | Tanouchi et al. . |
| 4,250,331 | 2/1981 | Shimshick . |
| 4,324,705 | 4/1982 | Sero et al. ........................... 521/44 |
| 4,345,098 | 8/1982 | Schep . |
| 4,355,175 | 10/1982 | Pusztaszeri ....................... 562/483 |
| 4,392,889 | 7/1983 | Grout .................................. 75/713 |
| 4,578,502 | 3/1986 | Cudmore ............................ 560/79 |
| 4,578,510 | 3/1986 | Doerr ................................ 562/483 |
| 4,602,046 | 7/1986 | Buser et al. ....................... 521/46 |
| 4,605,762 | 8/1986 | Mandoki ........................... 562/483 |
| 4,612,057 | 9/1986 | Buser et al. ......................... 134/13 |
| 4,620,032 | 10/1986 | Doerr ................................ 562/483 |
| 4,626,598 | 12/1986 | Packer et al. ..................... 562/487 |
| 5,064,466 | 11/1991 | Hilton ................................ 75/417 |
| 5,095,145 | 3/1992 | Rosen .............................. 562/483 |
| 5,120,768 | 6/1992 | Sisson ............................. 521/46.5 |

FOREIGN PATENT DOCUMENTS

| | | |
|---|---|---|
| 0497662A1 | 8/1992 | European Pat. Off. . |
| 0550979A2 | 7/1993 | European Pat. Off. . |
| 610135 | 10/1948 | United Kingdom . |

OTHER PUBLICATIONS

Research Disclosure Jan. 1981, p. 28, #20130, Silver Recovery and Polyester Recycling from Photographic Film Scarp; Clelland, et al.

Research Disclosure Dec. 1981, pp. 449–450, #21231, Separation of Polyvinylidene Chloride Copolymer Coatings from Oriented Polyester Substrates.

Primary Examiner—Samuel A. Acquah
Attorney, Agent, or Firm—Dority & Manning, P.A.

[57] ABSTRACT

A process for recycling polyester contained in waste materials is provided. The polyester is converted into a corresponding acid salt of a polybasic organic acid and a polyol. The process steps generally include first combining materials containing polyester with an alkaline composition to form a mixture. The mixture is heated, causing the polyester to convert to the acid salt and polyol. The polyol is evaporated and separated from the acid salt.

20 Claims, 1 Drawing Sheet

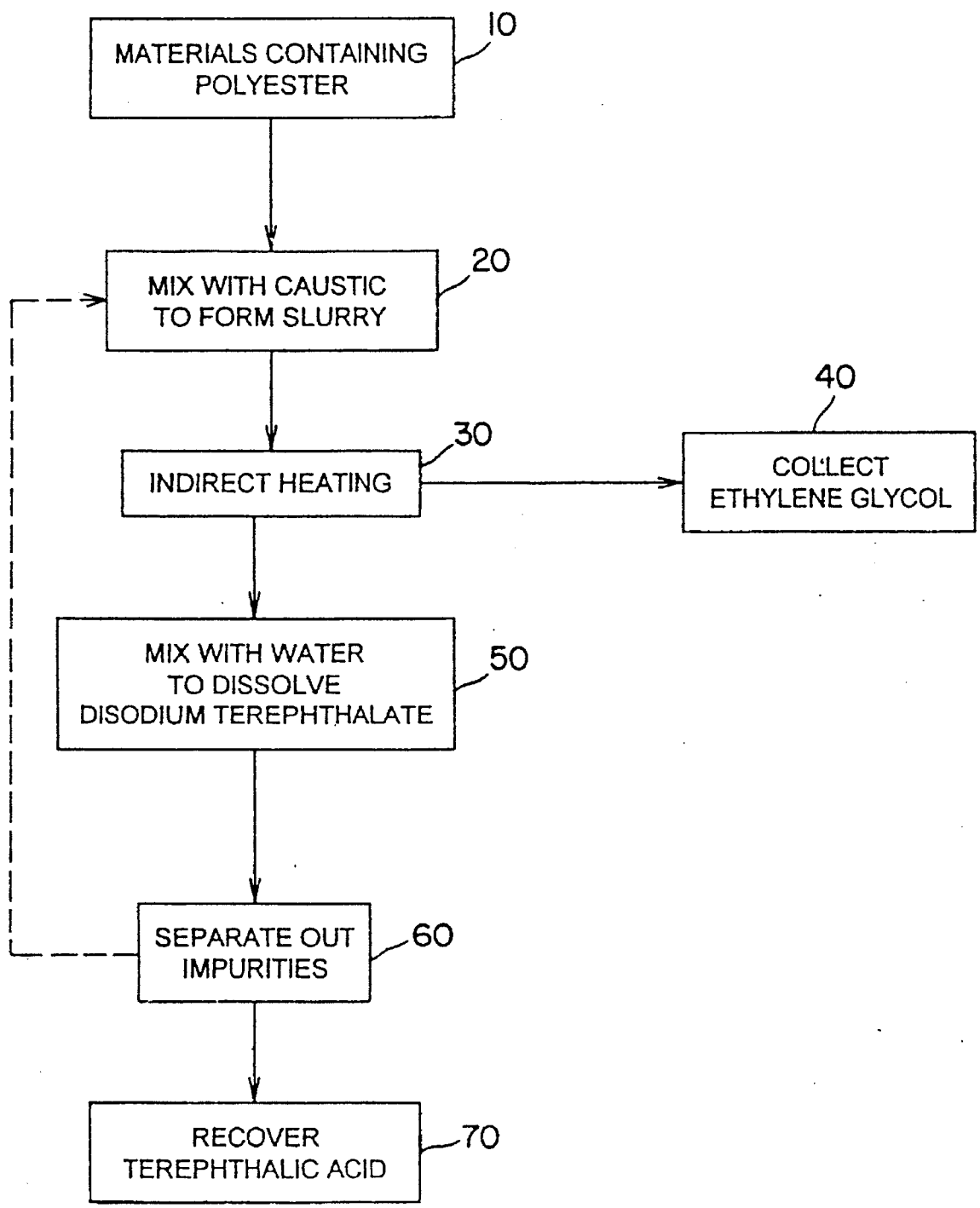

PROCESS FOR RECYCLING POLYESTERS

This application is a CIP of Ser. No. 08/234,237, filed Apr. 28, 1994, now U.S. Pat. No. 5,395,858.

BACKGROUND OF THE INVENTION

The present invention generally relates to a process for recycling polymeric materials and more particularly to a process for converting a polyester into its original chemical components.

Polyester is a polymeric material made from the esterification of polybasic organic acids with polyhydric acids. One exemplary polyester is manufactured by reacting terephthalic acid with ethylene glycol resulting in a compound known chemically as polyethylene terephthalate and commonly as PET. Widely known polyesters include Dacron and Mylar.

Polyeters are currently being used as a base material in a wide variety of applications. For example, polyester is commonly used to make photographic films, X-ray films, bases for magnetic coating such as in recording tapes, beverage containers, surgical aids such as synthetic arteries, and as a fabric for making garments and other similar items. However, although polyester is very useful, waste materials containing polyester are beginning to create a waste management and disposal problem.

Currently, those skilled in the art are seeking different methods of recovering and reusing polyester contained in waste plastic products. However, recovery of polyester from waste products has been found difficult. In particular, many prior art processes are not capable of efficiently or economically recovering polyester when a significant amount of impurities and contaminants are present. Such impurities include cellulosic materials, other polymeric materials and metals. As such, most attempts have been limited to mechanical recovery processes directed to specific polyester-containing materials. In these systems, the waste materials are merely washed in order to recover polyester films.

For example, U.S. Pat. No. 4,602,046 to Buser et al., discloses a method for the recovery of polyester from scrap material such as photographic film having a polyester base and at least one layer of macromolecular organic polymer. Specifically, scrap material is cut or chopped into small individual pieces or flakes and treated in a caustic alkaline solution at a solids level of at least 25% by volume and under conditions of high shear. The organic polymer coating material is removed from the polyester flakes. The polyester flakes are then separated from the polymer coating material by filtration or centrifugation, rinsed in water, and dried. The recovered polyester flakes can be used as a feed stock for making films, bottles or other polyester articles.

A method and apparatus for recovering silver and plastic from used film is also disclosed in U.S. Pat. No. 4,392,889 to Grout. In this method, the used film is first passed through a bath preferably comprising a hot caustic solution for precipitating silver layered on the film. The film then passes through a second bath of hot caustic until an adhesive sheet disposed on the film has been dissolved. Typically, the adhesive sheet is made of polyvinylidine chloride which adheres the silver to the film. After a second caustic bath, the film is dried and available for use.

A process for the recovery of clean polyester materials is disclosed in U.S. Pat. No. 3,928,253 to Thornton et al. Specifically, the process is directed to polyester photographic film, where the polyester is coated with binders, adhesives and metal compounds. In order to recover clean polyester, polyester photographic film is first wetted with an aqueous alkaline solution of an organic solvent which loosens and detaches coatings and subcoatings from the surface of the film. The polyester film is then separated from the reagent and rinsed. The reagent is then clarified and recycled and reused on other photographic film.

U.S. Pat. No. 3,652,466 to Hittel et al., discloses another process of recovering the polyester from polyester films. The coated films are cut into small pieces and treated with a caustic aqueous alkali solution to form a slurry. The slurry is fed into a classification column in which the pieces move downward countercurrent to a moving column of aqueous liquid which separates the pieces from the coating material. The pieces are removed from the bottom of the column in suspension and can thereafter be used as a source of polyester material. Further, the coating material can be removed from the top portion of the column and silver halide can be recovered in the form of silver.

Similarly, U.S. Pat. No. 3,647,422 to Wainer discloses the recovery of silver, polyester and amino acids from processed film and U.S. Pat. No. 3,873,314 to Woo et al. discloses the recovery of clean polyester materials from photographic film.

As shown above, the cited prior art methods of recovering waste polyester are generally limited to photographic films. In recycling the photographic films, silver is also recovered, thus making the processes economically viable. Mechanical recovery in non-silver containing polyester films presently lacks such economic advantages.

It has also been discovered that the prior art processes are generally further limited to processing particular types of films. Films containing higher proportionate amounts of non-polyester materials are typically much more difficult and expensive to process. For instance, many post consumer photographic films contain contaminants such as other polymeric materials in amounts up to about 50% by weight. These polymeric materials may include polyvinyl chloride, polyvinylidine chloride, acetate, polystyrene, polyethylene, and other polyolefins. Such films typically cannot be recycled and usually are discarded into landfills.

Recently the focus of recovering polyester from the waste stream has changed from mechanical washing processes to chemically converting the recovered polyester to more useful components. For instance, one current commercial process for chemically recycling polyester is methanolysis. This process is generally directed to the recycling of PET from X-ray and/or photographic film waste. The process involves the steps of: (1) sorting the film from other plastics and papers; (2) grinding the film; (3) washing the film with appropriate chemical solutions; (4) separating the film from a resulting sludge; (5) drying the film in the form of flakes; and (6) reacting the PET flakes with methanol under pressure, in order to convert it to ethylene glycol and dimethyl terephthalate (DMT). However, methanolysis is a very expensive process and can only be used with polyesters that are relatively free of contamination. In fact, many types of PET waste cannot be used due to the high impurity content.

Because of the deficiencies in the prior art, many waste products containing polyesters are not capable of being economically recycled. As such, most polyester waste products end up in landfills. In fact, millions of pounds of polyester-containing products are discarded in landfills each year. Landfill disposal is not only expensive, but is environmentally damaging.

Consequently, the prior art is generally deficient in providing an economical process for the recycling of polyesters.

The prior art is also deficient in providing a process capable of recycling polyesters from waste materials containing appreciable amounts of contaminants and impurities. Further, the prior art is generally deficient in providing a method for recycling polyesters from products other than photographic and X-ray films. Also, the prior art is generally deficient in providing a method of chemically recycling polyesters in which the polyester is converted into more usable chemical components, namely the raw materials from which the polyester is formed. Due to the increasing production of waste materials containing polyesters, it would be very desirable to have an economically viable process for recycling polyesters from the waste stream.

SUMMARY OF THE INVENTION

It is an object of the present invention to provide a process for recycling polyesters from waste materials.

It is another object of the present invention to provide a process for chemically recycling a polyester by converting it into chemical components.

Still another object of the present invention is to provide a process capable of recovering polyester from materials containing substantial amounts of impurities or contaminants.

It is another object of the present invention to provide a process for recycling polyesters without having to first mechanically wash the polyester in order to remove impurities.

Another object of the present invention is to provide a new process for recovering silver from polyester films such as photographic and X-ray films.

These and other objects of the present invention are achieved by providing a process for converting polyester into its original chemical reactants. The process involves the steps of combining materials containing polyester with an alkaline composition to form a mixture. The mixture is indirectly heated to a temperature sufficient to convert the polyester contained within the slurry to a corresponding acid salt and polyol. The heated mixture can then be mixed with a quantity of water sufficient to dissolve the acid salt and form an aqueous solution.

The process can further include the steps of vaporizing the polyol upon formation and separating it from the mixture. The evaporated polyol can then be condensed and collected. Also, the aqueous solution of the acid salt can be filtered as desired in order to remove any undissolved solids contained therein. Depending upon the salt, an acid can be added to the resulting filtrate in order to precipitate and recover a polybasic organic acid from the liquid.

In one embodiment, the alkaline composition combined with the materials containing polyester can be a 50% sodium hydroxide solution and can contain a surfactant or wetting agent. The alkaline composition can be mixed with the materials in a molar ratio of about two moles sodium hydroxide to about one mole of the polybasic organic acid contained within the polyester. The resulting slurry can be heated to at least the distillation temperature of the polyol. Preferably, this heating step is done in an oxygen-starved environment. Once heated, the mixture can then be mixed with a quantity of water such that the resulting aqueous solution contains from about 40% to about 90% by weight water.

These and other objects are also accomplished by providing a process for recycling waste materials containing polyester. The process includes contacting the waste materials containing a proportionate amount of polyester with a caustic solution of sodium hydroxide to form a slurry. The waste materials may also include contaminants such as organic impurities and metallic impurities. The slurry is heated to temperatures sufficient to saponify the polyester thereby forming a composition comprising a metal salt and a polyol. The composition is then further heated indirectly in order to evaporate the formed polyol and to carbonize any organic impurities present within the composition. The composition is heated at temperatures insufficient to significantly degrade the metal salt. The evaporated polyol is then separated from the composition.

The waste materials entering the process preferably contain at least about 30% by weight polyester. If the materials are contacted with a 50% sodium hydroxide solution, the weight ratio between the alkaline solution and the polyester contained within the waste materials can be about 1 to 1. A surfactant can also be added when forming the slurry.

Other objects, features and aspects of the present invention are discussed in greater detail below.

BRIEF DESCRIPTION OF THE DRAWING

A full and enabling disclosure of the present invention including the best mode thereof, to one of ordinary skill in the art, is set forth more particularly in the remainder of the specification, including reference to the accompanying figure, in which:

The Figure is a flow chart of one embodiment of the process of the present invention.

DETAILED DESCRIPTION OF PREFERRED EMBODIMENTS

The present invention is generally directed to a process for recycling polyesters. Using the process of the present invention, a polyester can be converted into its original chemical reactants. The process is primarily directed to using waste materials containing polyester, but is equally applicable to all known polyester-containing materials. Of particular advantage, the materials entering the process of the present invention need not be mechanically washed or chemically treated beforehand. Instead, any contaminants or impurities are separated and removed during the various processing steps. Further, if any valuable substances or metals are included within the contaminants and impurities, those substances can be removed and recovered.

As used herein, a polyester is defined as an esterification or reaction product between a polybasic organic acid and a polyol. It is believed that any known polyester or copolyester may be used in the process of the present invention. The polyester, when processed according to the present invention, is converted into its chemical components, namely a salt of the corresponding polybasic organic acid and the corresponding polyol. The process of the present invention is particularly directed to a class of polyesters referred to herein as polyol polyterephthalates, in which terephthalic acid serves as the polybasic organic acid.

As used herein, a polybasic organic acid refers to any organic acid having two or more carboxyl groups (—COOH). Most polyesters are derived from dibasic acids or, in other words, from dicarboxylic acids. Polybasic acids can have a linear or a cyclic conformation. Examples of linear polybasic acids that are sometimes used to make polyesters include the aliphatic dicarboxylic acids, and in particular the aliphatic dicarboxylic acids having up to ten carbon atoms in their chains. These acids include adipic acid, glutaric acid, succinic acid, malonic acid, oxalic acid, pimelic acid, suberic acid, azelaic acid, sebacic acid, maleic acid, and fumaric acid.

Cyclic polybasic organic acids, on the other hand, include the carbocyclic dicarboxylic acids. These acids are known as phthalic acid, isophthalic acid, and terephthalic acid. In particular, terephthalic acid is used to make polyethylene terephthalate which is perhaps the most commercially available polyester.

As described above, a polybasic organic acid is combined with a polyol to produce a polyester. Polyols are compounds that contain at least two hydroxyl groups. Many polyesters are synthesized using a polyol which only contains two hydroxyl groups, which are referred to as diols. Diols are normally prepared from an alkene by the net addition of two hydroxy groups to the double carbon bond in a method known as hydroxylation. Polyols are commonly referred to as glycols and polyhydric alcohols. Examples of polyols used to make polyesters include ethylene glycol, propylene glycol, butylene glycol, and cyclohexane dimethanol.

For exemplary purposes, the following table contains a nonexhaustive list of commercially available polyesters that may be converted or recycled according to the present invention. For each polyester, the corresponding polybasic organic acid and polyol are provided.

| POLYESTER | POLYBASIC ORGANIC ACID | DIOL |
| --- | --- | --- |
| Polyethylene Terephthalate | Terephthalic Acid | Ethylene Glycol |
| Polybutylene Terephthalate | Terephthalic Acid | Butylene Glycol |
| PETG Copolyester | Terephthalic Acid | Cyclohexane-dimethanol and Ethylene Glycol |
| PBTG Copolyester | Terephthalic Acid | Cyclohexane-dimethanol and Butylene Glycol |
| Polycyclohexane-dimethanol Terephthalate | Terephthalic Acid | Cyclohexane-dimethanol |

A very general summary of the process of the present invention includes first combining materials containing polyester with an alkaline compound to form a mixture. The mixture is heated, causing the polyester to hydrolyze, in part, into a metal salt (or acid salt) and a corresponding polyol. The polyol is volatilized and separated from the metal salt. The separated polyol is then condensed and collected for any use so desired.

The metal salt can also be collected and reused. In one embodiment, the metal salt and any other contaminants or impurities that may be present are combined and mixed with water in order to dissolve the salt (if the salt is water soluble). The resulting aqueous solution is then filtered in order to remove any undissolved impurities. In one embodiment, acid can be mixed with the resulting filtrate in order to convert and precipitate the salt as a polybasic organic acid. The polybasic acid can be separated from the solution, washed, dried and then used as desired in other processes and systems.

The process of the present invention can run continuously or can be set up as a batch system. Again, practically any material containing a polyester can be processed by the disclosed method. Preferably, the polyester materials are recovered from the solid waste stream, thus alleviating many environmental concerns and disposal problems. Representative materials that can be used in the present invention include but are not limited to developed or undeveloped photographic film and X-ray film, plastic bottles and containers, polymeric adhesive films, saran-bearing polyester films, papers containing polyester, and even polyester and polyester blend fabrics. Currently, such products are being disposed of in landfills after use.

Preferably, the materials contain about thirty percent (30%) by weight polyester or greater, although any materials containing polyester can be processed according to the present method. In particular, blended fabrics containing 40% or 50% polyester may be used in the present process.

The process of the present invention will now be described in more detail. First, depending on the variety and composition of the materials, the materials selected for use in the present invention can be chopped or ground into a particular size. For instance, if recyling photographic film, the film is preferably cut to an average dimension of less than about one inch. Generally, the smaller the size of the material, the less retention time is needed within the process. However, all different sizes and shapes of material may be used within the system of the present invention and no one size or shape is required.

After being sized, the polyester containing materials are combined and mixed with an alkaline composition to form a mixture. For proper mixing, the materials can be fed to a mixing tank such as a ribbon blender or the like. Preferably, an alkaline solution is combined with the materials to form a slurry. A caustic powder or molten caustic, however, can also be blended with the materials. If a powder is used, it may be necessary to preheat the mixture.

The alkaline compound selected for mixing with the materials preferably is sodium hydroxide, known commonly as caustic soda. Other metal hydroxides, however, can be used. Such compounds include calcium hydroxide, magnesium hydroxide or potassium hydroxide. When used in solution, the metal hydroxide can be combined with water prior to mixing with the materials containing the polyester. Although concentration is generally not a critical factor, the metal hydroxide can be mixed with water in about a 1 to 1 ratio.

Regardless, the metal hydroxide should be added to the polyester containing materials such that the metal contained within the hydroxide and the polybasic organic acid are added in stoichiometric amounts. For instance, if the polyester is a polyol polyterephthalate, and the hydroxide contains an alkali metal, the molar ratio of hydroxide to polyester should be at least 2 to 1. If an alkaline earth metal hydroxide is used, however, the molar ratio should be about 1 to 1 or greater. Preferably, the hydroxide is added in excess to ensure a complete reaction.

The materials and the alkaline can be initially combined at ambient temperature and pressure. At this stage in the process, the temperature can be increased, although not necessary.

Optionally, a surfactant or wetting agent may be added to the materials and the alkaline when forming the mixture. Addition of a surfactant may facilitate the mixing of the alkaline with the materials in order to produce a more uniform blend. The surfactant should be alkaline stable and can be anionic in character. An example of a suitable surfactant is SURMAX CS727 sold by Chemax, Inc. of Greenville, S.C.

After thorough and complete mixing to ensure substantial uniformity, the mixture is heated, and preferably heated indirectly such that it does not contact an open flame. Heating the mixture serves a number of purposes within the process. First, heating causes the polyester contained within the mixture to hydrolyze or, more specifically, to saponify. As used herein, saponification is the conversion of an ester heated in the presence of an alkaline into the corresponding polyol and acid salt.

The formed acid salt or metal salt produced by the reaction is usually a solid and typically has the appearance of a flake. Polyols typically are liquids at room temperature.

Besides hydrolyzing and saponifying the polyester, the mixture can also be heated to temperatures sufficient to volatilize, or evaporate, the above-formed polyol. Consequently, preferably the formed acid salt has a melting point that is higher than the boiling point of the corresponding polyol. The metal hydroxide combined with the polyester should be selected to meet this condition whenever possible. The process of the present invention remains relatively simple if the metal salt remains a solid through the heating phase of the process. After vaporizing the polyol, it can be easily separated from the remaining product stream containing the acid salt.

Consequently, the mixture should be heated to at least the distillation temperature of the polyol. At these temperatures, unexpectedly, the acid salt does not burn, or otherwise significantly degrade. As used herein, the term degrade refers to burning, or otherwise changing the physical and chemical characteristics of a substance. However, at these same temperatures, any organic impurities or contaminants present within the product stream can be carbonized. Such impurities would include paper and other wood products, fatty acids, gelatines, natural fibers such as cotton, polymers such as polyvinyl chloride, polyvinylidene chloride, cellulose acetate, polystyrene, etc. and other combustibles. Upon carbonization, the organic impurities, and particularly the low molecular weight impurities, decompose resulting in a flue gas which also separates from the product stream.

The actual temperature to which the mixture is heated depends upon a number of factors. For instance, each particular polyol will have a separate and distinct distillation temperature range. Also, the temperatures may depend upon the types of contaminants present within the mixture and the requirements for carbonizing those contaminants. Another factor to consider is the melting point of the acid salt. When processing a polyol polyterephthalate, at atmospheric pressure, it has been found optimal to heat the mixture to at least 400° F.

Also, the mixture is preferably heated in an oxygen-starved environment. As used herein, oxygen-starved refers to an environment in which oxygen is present below about 19% by volume. Maintaining lower oxygen levels during the heating phase not only protects the acid salt from being degraded but also prevents against uncontrolled combustion. In particular, oxygen levels should remain lower when cotton, acetate or other flammable substances are present in the materials. However, enough oxygen should be present for carbonization to occur when desired. It is believed that oxygen levels should be around 5% when substantial amounts of impurities are present.

One method of maintaining lower oxygen levels can include decreasing air flow around the mixture during heating. In another embodiment a blanket of inert gas, such as nitrogen, can be applied to the mixture. Also, the mixture can be heated at reduced pressures corresponding to lower oxygen levels. Reducing the pressure also has the added advantage of reducing the temperature requirements needed for evaporating the polyol. In essence, reducing the pressure lowers the distillation temperature range of the polyol.

Many different and various machinery and processing equipment can be used to heat the alkaline and polyester mixture. As described above, preferably the mixture is heated indirectly. As such, a heater should be chosen that does not subject its contents to an open flame. Suitable examples of heating devices that can be used in the process of the present invention include ovens, kilns and thermal processors which use hot oil or electrical heating elements to heat their contents. For instance, the Renneburg Division of Heyl and Patterson, Inc. in Pittsburgh, Pa. is currently marketing a multi-disc thermal processor. In this device, heat transfer fluids are circulated within hollow disks. A product stream is heated indirectly when contacted with these discs. Of course, many other similar devices are available which may be used in the process of the present invention.

In one embodiment, the mixture can be heated in a rotary kiln. The rotary kiln can be heated by an electrical element, by heated oil or by fossil fuel burners. The kiln can be heated to a predetermined temperature while air flow is controlled therethrough. One example of a suitable indirectly heated kiln for use with the process of the present invention is the Rotary Calciner also marketed by the Renneburg Division of Heyl and Patterson, Inc. Specifically, a Rotary Calciner was successfully tested for use in the process of the present invention.

In another embodiment, the mixture can be heated in a staged system. In this embodiment, the mixture is first heated to a temperature at which the polyol begins to evaporate or distill and at reduced pressure. Retention times at this stage of heating should be longer for allowing all of the formed polyol to evaporate. In other words, retention times should be long enough to overcome the diffusion coefficient of the polyol from the acid salt particulate.

After all of the polyol has evaporated, the product stream can then be transferred to a second stage heater. In the second stage, the product stream is heated to at least the carbonization temperature of the combustibles contained therein but at a temperature insufficient to degrade the salt of the polyorganic acid. The second stage can be carried out using a separate heating device or by using a single heating device with different temperature zones.

During the heating step, the polyol can be evaporated and collected. Specifically, the polyol can be collected using an appropriate vapor collection device such as a condenser. The recycled polyol can then be used as desired.

The product stream separated from the gas or vapor stream is then collected from the heater. At this point, the product stream includes the acid salt and may contain metal contaminants, the byproducts of carbonization, and other impurities. In one embodiment, the product stream is fed to a mixing tank such as a quench tank and mixed with water in order to dissolve the acid salt, if the acid salt is water soluble. The water solubility of the acid salt may depend upon the metal hydroxide selected for mixing with the polyester. Consequently, if water solubility is desired, a metal hydroxide should be chosen that will achieve this result.

When mixed with water, the acid salt or metal salt dissolves along with any other salts present in the product stream. However, water insoluble contaminants such as metal's, uncarbonized impurities, carbonized organic matter, or unreacted polyester do not dissolve and can be separated from the aqueous solution. This can be done by well known separation techniques such as filtration or centrifugation.

The resulting filter cake filtered from the aqueous solution contains all of the undissolved impurities and contaminants. The filter cake can be discarded or can be incinerated. However, if any useful materials are present within the filter cake, they can be separated and recovered. For instance, developed and undeveloped photographic films contain silver which is considered a precious metal. If silver-bearing materials enter into the process of the present invention, the silver will be collected in this filter cake. In one embodiment, the filter cake can be roasted in a kiln at high temperatures such as around 1500° C. to incinerate most of the composition and leave behind silver powder. As such, the present invention is also directed to a new and useful process for the recovery of silver from polyester materials. Of course, the silver can also be separated by other means as can be appreciated by one skilled in the art.

After separating out the undissolved impurities, the resulting aqueous filtrate comprises water, the dissolved acid salt and any other dissolved salts. Depending upon the content of the starting materials used in the process, the filtrate can be used in other processes without further treatment. The acid salt in most circumstances, can also be precipitated and recovered from the solution.

In one exemplary embodiment of the present invention, the polyester fed into the process is polyethelyene terephthalate (PET). PET, one of the most widely available polyesters, is formed from the esterification between terephthalic acid, a polybasic organic acid, and ethylene glycol, a diol. Using the process of the present invention, PET can be recycled and converted into its original chemical reactants.

Referring to the Figure, a process according to the present invention for converting PET into terephthalic acid and ethylene glycol is illustrated on a flow chart. As shown, materials containing polyesters 10 are first provided. Materials 10 can include a wide variety and mixture of articles and can be recovered from the solid waste stream or from other sources. Preferably, the materials contain at least 30 percent by weight PET. If necessary, the materials can first be sized or pretreated.

As shown in the Figure, materials 10 are combined with an alkaline composition, such as a solution to form a slurry 20. Although other metal hydroxides may be used, slurry 20 is preferably formed using a caustic soda solution. The caustic soda solution should be added to materials 10 in quantities such that the molar ratio of caustic soda to terephthalic acid contained within the polyester is about 2 to 1. Conveniently, when using a 50 percent by weight caustic solution, the weight ratio between the caustic soda solution and the polyester contained within the materials is normally about 1 to 1 . However, depending upon the substances present in materials 10 more or less caustic soda may be added to form slurry 20. Sufficient sodium hydroxide should be present to support a complete reaction with the polyester contained in materials 10.

When forming slurry 20, as stated above, a surfactant or wetting agent may also be added to the mixture. Addition of a surfactant may facilitate the mixing of the alkaline solution with materials 10.

After thorough and complete mixing, slurry 20 is heated, and preferably heated indirectly as shown at 30. Heating slurry 20 causes the PET contained within the slurry to hydrolyze or saponify. The PET is converted to disodium terephthalate and ethylene glycol.

Disodium terephthalate produced by the reaction typically has the appearance of a white or tan solid and is water soluble. Ethylene glycol, on the other hand, is a liquid at room temperature. Slurry 20, however, as shown in the figure is heated to a temperature sufficient to volatilize, or evaporate, the formed ethylene glycol. Consequently, slurry 20 should be heated to at least the distillation temperature of ethylene glycol.

If impurities are present within slurry 20, the slurry can be heated to temperatures capable of carbonizing organic impurities, contaminants and other combustibles. Upon carbonization, the combustibles are decomposed, resulting in a flue gas which separates from slurry 20.

Unexpectedly, at temperatures capable of evaporating ethylene glycol and at temperatures capable of carbonizing combustibles, the disodium terephthalate does not burn, melt or otherwise significantly degrade. This surprising discovery makes it possible to separate and recover the disodium salt from the glycol and from the combustibles.

In summary, indirectly heating slurry 20 causes the polyester contained in materials 10 to saponify, resulting in the formation of disodium terephthalate particulate and ethylene glycol. Further, slurry 20 is heated to temperatures sufficient to evaporate the formed ethylene glycol and separate it from the products stream containing the disodium terephthalate. Also, during this heating step, organic impurities present within slurry 20 can be carbonized causing them to decompose.

Preferably, slurry 20 is heated to temperatures capable of volatilizing the ethylene glycol, but at temperatures insufficient to degrade the disodium terephthalate. Specifically, at atmospheric pressure, slurry 20 is optimumly heated to temperatures between from about 400° F. to about 600° F. and preferably between from about 450° F. to about 550° F. Of course, optimal temperatures will depend upon the systems conditions and upon the existing pressures. For instance, if slurry 20 were heated at reduced pressures, the temperature requirements may be lower.

Slurry 20 can be heated in various devices. For instance, in one embodiment, slurry 20 can be heated in a rotary kiln. Specifically, a Rotary Calciner marketed by the Rennburg Division of Heyl and Patterson, Inc. was successfully tested for use in the process of the present invention. The Calciner had a 2 foot 6 inch diameter, was 32 feet long, and was heated with an electrical element. Adequate retention times of slurry 20 within the kiln were found to be about 30 to 40 minutes. Of course, if other types of heating equipment were used in the process of the present invention, retention times and other process parameters may be modified.

As described above, while slurry 20 is being heated, evaporated ethylene glycol, any flue gas created by the carbonization of organic contaminants, and water vapor are given off and separated from the product stream. This gaseous composition can then be collected and processed in order to remove and isolate the ethylene glycol as illustrated at 40.

The collected ethylene glycol is a compound used in many processes and applications. Specifically, ethylene glycol is commonly used as an anti-freezing agent and, of course, can also be used to manufacture PET or other polyesters.

Many different methods for collecting a vapor such as ethylene glycol from a gas stream exist. In one embodiment, the gas stream separated from the product stream of the present invention can be fed to a suitable condenser. Specifically, a partial condenser can be used in which only the ethylene glycol will condense and be collected from the gas stream. The remaining flue gas and water vapor can then be sent to a scrubber or otherwise discharged according to environmental regulations. The liquid ethylene glycol can then be used for other applications as desired.

Once the ethylene glycol is separated and collected, the resulting product stream can be removed from the heating source and further processed. At this point, the product stream contains disodium terephthalate and possibly contaminants and other impurities. As shown in the Figure, in one embodiment, the product stream can be mixed with water in order to dissolve the disodium terephthalate as illustrated at 50.

When mixed with water, the disodium terephthalate dissolves along with any other salts present in the product stream. Water insoluble contaminants, such as metals, uncarbonized impurities, carbonized organic matter, or unreacted polyester do not dissolve and can be separated from the aqueous solution. The amount of water to be mixed with the product stream varies depending upon the composition of the product stream and the amount of disodium terephthalate present. Specifically, the appropriate amount of water to add can be up to about 90 percent by weight of the resulting aqueous solution. Under most circumstances, the water should be around 80 percent by weight of the solution.

After mixing the product stream with water, the insoluble contaminants can be separated from the aqueous solution as illustrated at 60. Any known separation technique may be used including filtration or centrifugation.

Once the insoluble impurities are separated from the aqueous solution, the impurities can be either discarded or, if a useful material is present, can be further processed. For instance, as described above, if silver is present within the solids, the material can be roasted in order to recover silver powder.

After separating out the undissolved impurities, the resulting aqueous filtrate comprises water, dissolved terephthalate and any other dissolved salts. If desired, terephthalic acid can be recovered from the solution as is shown at 70. For instance, the filtrate can be acidified causing terephthalic acid of high purity to be precipitated. In order to acidify the filtrate, a mineral acid such as hydrochloric acid, phosphoric acid or sulfuric acid or a strong organic acid such as acetic acid can be added to the solution. Once the terephthalic acid precipitates, the terephthalic acid can be filtered, washed and dried, leaving a relatively pure product.

The remaining filtrate solution, removed from the precipitate, contains water and, possibly, some salts such as sodium chloride. This solution can be further treated and disposed. Also, the sodium salt can be recovered and reused if desired.

It is to be understood that the above description is a description of a preferred embodiment of the process of the present invention and does not embrace all variables that may be practiced. For instance, other optional steps can be added to the process in order to enhance performance and to achieve a desired result. For instance, while the process is preferably carried out in a continuous manner, a batch system may be just as effective. In one embodiment, a pan may be used to heat slurry 20 to the required temperatures inside of an oven. However, in a batch system, retention times may increase and the quantity of material being processed at a particular time may have to be decreased.

Another option for the process of the present invention is to include a recycle or return stream as shown in phantom in the Figure in order to further purify the resulting products. For instance, the undissolved impurities and contaminants separated from the aqueous filtrate could be mixed with more caustic to form a slurry and then processed as before. By running these solids through the process multiple times, the concentration of impurities, such as silver, will increase in the filter cake. Further, a higher percentage of the polyester contained in materials 10 may be processed.

In another embodiment, an activated carbon filter can be used to filter the aqueous solution of disodium terephthalate. Use of a carbon filter is well known and will further purify the aqueous filtrate.

Besides PET, other polyesters including other polyol polyterephthalates can also be chemically converted similar to the procedures described above. For instance, another commercially available polyester is polybutylene terephthalate. Similar to the process described above, polybutylene terephthalate can be blended with an alkaline composition and heated causing saponification. As opposed to PET, polybutylene terephthalate, when using caustic soda, converts to butylene glycol and, again, disodium terephthalate. The butylene glycol can be evaporated and recovered while the disodium terephthalate can ultimately be collected as terephthalic acid.

The present invention may be better understood by reference to the following examples.

EXAMPLE I

The following example demonstrates the recovery and conversion of PET from waste materials.

Four Hundred and Sixty-five (465) pounds of developed lithographic film were ground to an average dimension of 3 to 10 millimeters and continuously fed into a process in accordance with the present invention. The ground lithographic film was first added to a ribbon blender and mixed with 488 pounds of 50% caustic soda and water and 0.2 pounds of an alkaline stable anionic surfactant. The ribbon blender used was the Horizontal Blender #250 sold by Young Industries of Muncy, Pa. The surfactant was SURMAX CS727 sold by Chemax, Inc. of Greenville, S.C. The film, the caustic soda and the surfactant were mixed until the film was evenly coated.

From the ribbon blender, the mixture was then fed into an externally heated rotary kiln via a screw conveyor. The rotary kiln used was the above described Rotary Calciner sold by Heyl & Patterson, Inc., Renneburg Division of Pittsburgh, Pa. The shell temperature of the rotary kiln was maintained at 550° F. The polyester contained in the film was converted into ethylene glycol and disodium terephthalate. The ethylene glycol that was formed was evaporated and was removed from the kiln by flowing air therethrough. Ultimately, the ethylene glycol was condensed and collected using a partial condenser. Water vapor produced within the kiln was allowed to pass through the condenser and into a scrubber system. One Hundred and Sixty (160) pounds of ethylene glycol were collected. The retention time of the mixture in the heated zone of the kiln was approximately 30 minutes.

The resultant solid material from the kiln was in the form of a tan granular powder. The yield of solid material from the kiln was 475 pounds. This material was added to 1900 pounds of water in order to dissolve the disodium terephthalate. The aqueous solution was then passed through a filter in order to remove any undissolved impurities.

The filter cake, after being dried, weighed 56 pounds and contained 9% by weight silver. The filter cake was then roasted at 1250° F. and smelted in order to recover pure silver.

Five Hundred and nineteen (519) pounds of 32% hydrochloric acid was then added to the filtrate in order to adjust the pH to 3.5. A precipitate formed as the acid was added. This precipitate was removed using a filter and washed with 1000 pounds of fresh water. After drying, the precipitate was analyzed and found to be at least 98% terephthalic acid. The yield of terephthalic acid was 370 pounds.

EXAMPLE II

The process of the present invention was also tested in a batch system. Specifically, 84 pounds of nonsilver-bearing PET film coated with an adhesive polymer formed from copolymers of polyvinylidene chloride and polyvinyl chloride were ground to an average dimension of about 1 to 2 millimeters. The ground PET film was charged to a mixer and 42 pounds of dry caustic soda and 32 pounds of water were added. Mixing was continued until the film was evenly coated. This mixture was then added to a steel pan and placed in an oven at 450° F. for two hours. Ethylene glycol vapor and other gases given off during heating were removed from the oven by an air sweep and passed to a scrubber system.

The remaining solid product in the pan after heating weighed 94 pounds. This product was added to 375 pounds of water and filtered. After drying, the filter cake weighed 2.5 pounds. Seventy-eight (78) pounds of 32% hydrochloric acid was then added to the filtrate to adjust the pH to 3.5. A white/tan precipitate formed as the acid was added. The precipitate was removed by filtration and washed with 200 pounds of fresh water. After being dried, the precipitate was analyzed and found to be at least 98% terephthalic acid. The yield of terephthalic acid was 68 pounds.

EXAMPLE III

The following test was performed in order to ensure that polyester cloth materials (containing PET) can also be processed in accordance with the present invention. Specifically, 26.8 parts of blue wipes were cut into approximately ½" squares. A blue wipe is a fabric made from a blend of polyester and paper. The cut blue wipe squares were combined and mixed with 26.8 parts of a 50% sodium hydroxide solution, 0.2 parts of the SURMAX CS727 surfactant used in Example I and 10 parts of water. The resulting slurry was placed in an oven at 300° C. for 30 minutes. After 30 minutes, the paper was charred and appeared to have burned.

After heating, the resultant material was mixed with water and filtered. The filtrate was acidified, causing a white precipitate to form. The precipitate was analyzed and found to be terephthalic acid.

It will be understood that the invention is not limited to any specific parameters, amounts or process steps described herein, and that any method employing agents equivalent to those described falls within the scope of the present invention. It will be understood that while the form of the invention shown and described herein constitutes a preferred embodiment of the invention, it is not intended to illustrate all possible forms of the invention. In addition, it should be understood that aspects of the various embodiments may be interchanged both in whole or in part. The words used are words of description rather than of limitation. Various changes and variations may be made to the present invention without departing from the spirit and scope of the following claims.

What is claimed:

1. A process for recycling and converting polyester into usable chemical components, said process comprising the steps of:

combining materials containing polyester with an alkaline composition to form a mixture;

heating said mixture to a temperature sufficient to convert said polyester contained within said materials to a corresponding acid salt of a polybasic organic acid and a polyol, said mixture being heated to at least the distillation temperature of said polyol for evaporating said polyol; and separating said evaporated polyol from said acid salt.

2. The process as defined in claim 1, wherein said polyester is polyethylene terephthalate and said corresponding acid salt and polyol are a metal terephthalate and ethylene glycol respectively.

3. The process as defined in claim 1, wherein said polyester is polybutylene terephthalate and said corresponding acid salt and polyol are a metal terephthalate and butylene glycol respectively.

4. The process as defined in claim 1, wherein a surfactant is also combined with said materials and said alkaline composition when forming said mixture.

5. The process as defined in claim 1, wherein said mixture is heated to at least 400° F.

6. The process as defined in claim 1, wherein said evaporated polyol is condensed and collected.

7. The process as defined in claim 1, wherein said alkaline composition contains a metal hydroxide, said metal hydroxide being selected from the group consisting of sodium hydroxide, calcium hydroxide, magnesium hydroxide, and potassium hydroxide.

8. The process as defined in claim 1, wherein said mixture is heated in an oxygen starved environment.

9. The process as defined in claim 1, wherein said acid salt has a melting point that is higher than the boiling point of said polyol.

10. A process for recycling and converting polyester into usable chemical components, said process comprising the steps of:

providing materials containing a proportionate amount of a polyester, said polyester comprising a polyol polyterephthalate;

blending said materials with an alkaline composition to form a mixture;

indirectly heating said mixture to saponify said polyester contained in said materials, said polyester being converted to a corresponding metal terephthalate and a polyol; and evaporating and separating said polyol from said metal terephthalate.

11. The process as defined in claim 10, wherein said alkaline composition contains sodium hydroxide and wherein, upon heating, said polyester is converted to said polyol and disodium terephthalate.

12. The process as defined in claim 10, further comprising the step of carbonizing any organic impurities present within said materials.

13. The process as defined in claim 12, wherein said mixture is heated to at least 400° F. in order to carbonize said organic impurities.

14. The process as defined in claim 10, further comprising the step of condensing and collecting the separated polyol.

15. The process as defined in claim 12, further comprising the steps of:

dissolving said metal terephthalate in an aqueous solution;

filtering said aqueous solution in order to remove any undissolved impurities;

precipitating terephthalic acid from said aqueous solution; and separating said precipitated terephthalic acid from said solution.

16. A process for recycling and converting polyethylene terephthalate into usable chemical components, said process comprising the steps of:

combining materials containing polyethylene terephthalate with an alkaline composition to form a mixture;

heating said mixture to a temperature sufficient to convert said polyester contained within said materials to a metal terephthalate salt, water and ethylene glycol, said temperature being at least at the distillation temperature of said ethylene glycol for evaporating said formed ethylene glycol and said water; and separating said evaporated ethylene glycol and water from a product stream containing said metal terephthalate salt.

17. The process as defined in claim 16, wherein said alkaline composition is a sodium hydroxide solution.

18. The process as defined in claim 16, wherein said mixture is also heated to a temperature sufficient to carbonize any organic impurities present within said materials.

19. The process as defined in claim 18, wherein said mixture is heated to at least 400° F. in an oxygen starved environment.

20. The process as defined in claim 16, further comprising the steps of:

combining said product stream with a solvent, said solvent dissolving said metal terephthalate salt to form a solution;

filtering said solution to remove any undissolved contaminants; and precipitating and recovering terephthalic acid from said solution.

* * * * *